(12) United States Patent
Arenson et al.

(10) Patent No.: US 7,649,974 B2
(45) Date of Patent: Jan. 19, 2010

(54) METHOD AND SYSTEM FOR CONTROLLING AN X-RAY IMAGING SYSTEM

(75) Inventors: Jerome Stephen Arenson, Haifa (IL); David Ruimi, Netanya (IL); Oded Meirav, Haifa (IL); Robert Harry Armstrong, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 1266 days.

(21) Appl. No.: 10/993,705

(22) Filed: Nov. 18, 2004

(65) Prior Publication Data

US 2006/0104496 A1    May 18, 2006

(51) Int. Cl.
*H05G 1/26* (2006.01)
*G01N 23/00* (2006.01)

(52) U.S. Cl. ............................................. 378/16; 378/5
(58) Field of Classification Search ................. 378/4–20
See application file for complete search history.

(56) References Cited

U.S. PATENT DOCUMENTS

| | | | |
|---|---|---|---|
| 5,165,100 A | 11/1992 | Hsieh et al. | |
| 2004/0102688 A1* | 5/2004 | Walker et al. | 600/407 |

* cited by examiner

*Primary Examiner*—Hoon Song
(74) *Attorney, Agent, or Firm*—Armstrong Teasdale LLP

(57) ABSTRACT

Methods and systems for controlling an X-ray imaging system. The method for controlling an X-ray imaging system includes acquiring a plurality of subviews of patient attenuation data wherein a first set of subviews of patient attenuation data is acquired at a first radiation flux level and a second set of subviews of patient attenuation data is acquired at a second radiation flux level. The first radiation flux level is different than the second radiation flux level. The method further includes combining the first set of subviews of patient attenuation data and the second set of subviews of patient attenuation data to form corrected views for subsequent image generation.

52 Claims, 5 Drawing Sheets

METHOD AND SYSTEM FOR CONTROLLING AN X-RAY IMAGING SYSTEM

BACKGROUND OF THE INVENTION

This invention relates generally to X-ray imaging systems and more particularly, to methods of controlling X-ray imaging systems.

In X-ray imaging systems, detector systems may be exposed to a wide range of X-ray radiation fluxes during an exposure that may be due to variations in a patient anatomy and variable X-ray acquisition settings. The wide range of the X-ray flux may require a detector system with a large dynamic range such that the detector system response to relatively high X-ray flux and relatively low X-ray flux are both within predetermined specifications. At least some known X-ray imaging systems use techniques such as surrounding the patient with a water bag or placing "bowtie" filters in the X-ray beam to reduce the required dynamic range of the detector systems. The "bowtie" filters are placed in the X-ray beam to selectively shape the X-ray beam radiation flux to inversely match the patient cross-section. Further, more radiation flux is provided through thicker parts and less radiation flux is provided through thinner parts of the patient anatomy. This results in a more uniform radiation flux profile and reduces the detector dynamic range required.

However, the known detector systems may still require a minimum dynamic range of at least 1,000,000:1 to adequately detect the variations in the X-ray radiation fluxes impinging on the detector systems.

BRIEF DESCRIPTION OF THE INVENTION

In one exemplary embodiment, a method for controlling an X-ray imaging system is provided. The method includes acquiring a plurality of subviews of patient attenuation data wherein a first set of subviews of the patient attenuation data is acquired at a first radiation flux level and a second set of subviews of the patient attenuation data is acquired at a second radiation flux level. The first radiation flux level is different than the second radiation flux level. The method further includes combining the first set of subviews of the patient attenuation data and the second set of subviews of the patient attenuation data to form corrected views for subsequent image generation.

In another exemplary embodiment, an X-ray imaging system is provided. The system includes a gantry including a detector system and an X-ray source for radiating an X-ray beam along an imaging plane and/or volume towards the detector system. The system further includes at least one of an mA controller and a high voltage controller for controlling electrical energy to the X-ray source and a modulation controller communicatively coupled to at least one of the mA controller and the high voltage controller. The modulation controller is configured to generate timing signals for controlling at least one of mA controller and a high voltage controller. The system further includes a computer coupled to the X-ray source and the gantry. The computer is programmed to control the X-ray imaging system to acquire a plurality of subviews of patient attenuation data wherein a first set of subviews of the patient attenuation data is acquired at a first radiation flux level and a second set of subviews of the patient attenuation data is acquired at a second radiation flux level. The first radiation flux level is different than the second radiation flux level. The computer is programmed further to control the X-ray imaging system to combine the first set of subviews of the patient attenuation data and the second set of subviews of the patient attenuation data to form corrected views for subsequent image generation.

DETAILED DESCRIPTION OF THE INVENTION

Various embodiments of the invention provide a method for controlling an X-ray imaging system. The X-ray imaging system may be, for example, a Computer Tomography (CT) scanner, and/or an X-ray scanner.

Figure 1:
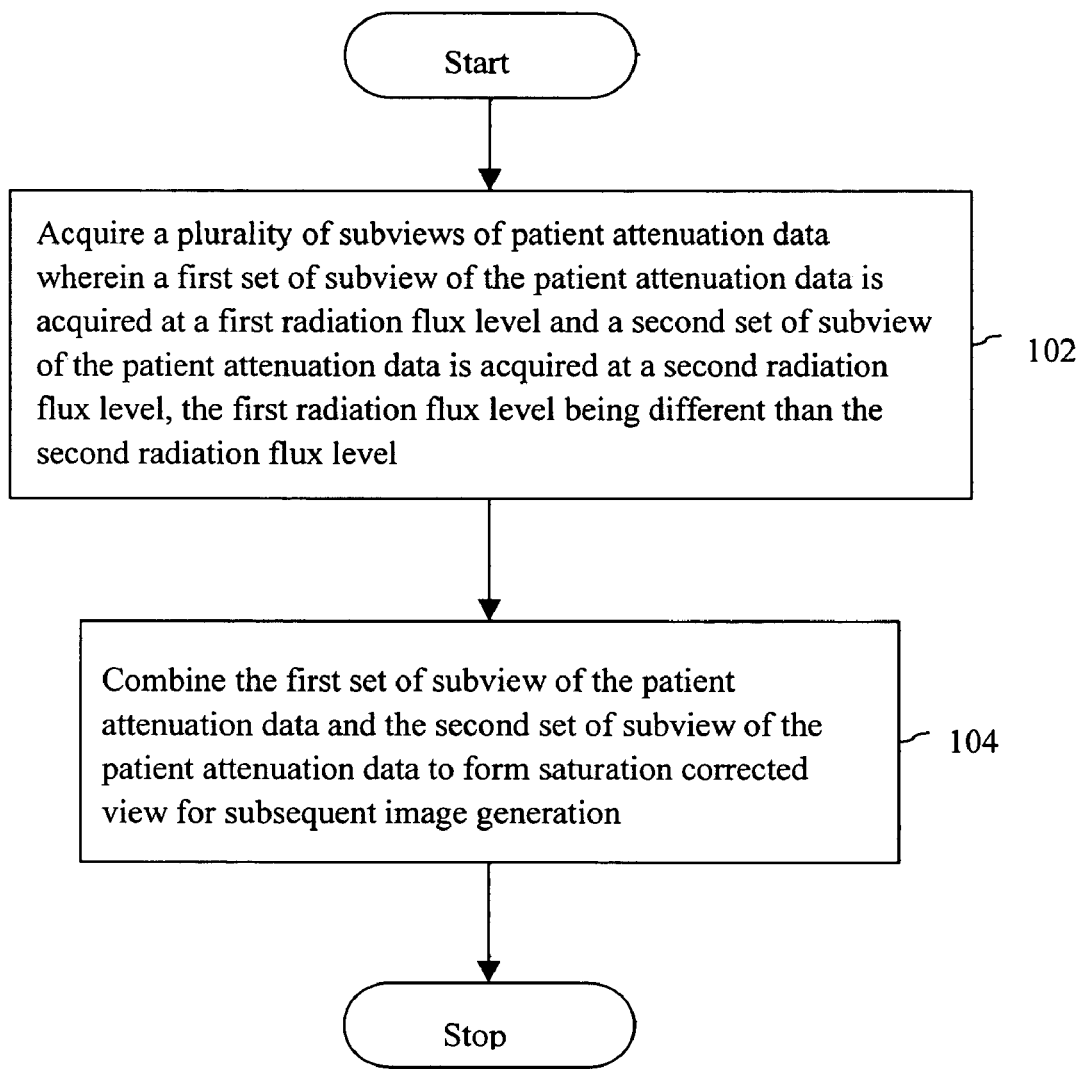
FIG. 1 is a flowchart illustrating a method for controlling an X-ray imaging system in accordance with an exemplary embodiment of the invention.

FIG. 1 is a flowchart illustrating a method for controlling an X-ray imaging system in accordance with an exemplary embodiment of the invention. At 102, a plurality of subviews of patient attenuation data is acquired at different radiation flux. A first set of subviews of the patient attenuation data is acquired corresponding to a first radiation flux level and a second set of subviews of the patient attenuation data is acquired corresponding to a second radiation flux level, wherein the first radiation flux level is different than the second radiation flux level. At 104, the first set of subviews and second set of subviews of the patient attenuation data are combined to form saturation corrected views for subsequent image generation. The saturation may occur for values of radiation flux that lie outside a dynamic range of a detector system of the X-ray imaging system.

In various embodiments of the invention, the plurality of subviews is acquired using the CT scanner. The various embodiments of the invention are applicable to both helical and non-helical scanning of the CT scanner, single and multi-detector CT scanners, and third, fourth and subsequent generations CT scanners, and other CT scanner configurations.

Figure 2:
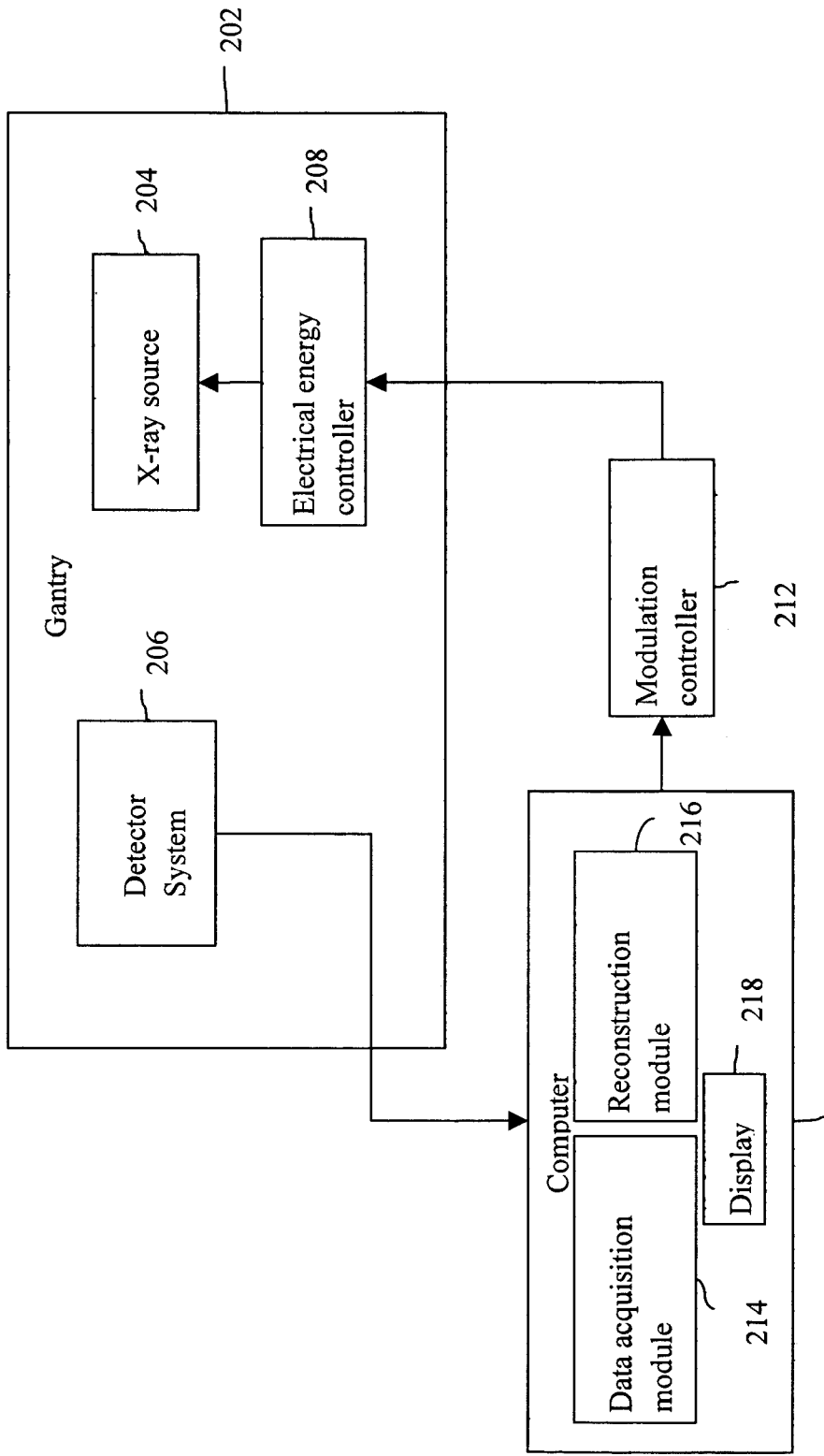
FIG. 2 is a block diagram of an X-ray imaging system in accordance with an exemplary embodiment of the invention.

FIG. 2 shows an X-ray imaging system 200 in accordance with an exemplary embodiment of the invention. X-ray imaging system 200 includes a gantry 202. Gantry 202 includes an X-ray source 204, a detector system 206, and an electrical energy controller 208. X-ray imaging system 200 further includes a computer 210, and a modulation controller 212.

In operation, X-ray source 204 radiates an X-ray beam along an imaging plane and/or volume towards detector system 206, which measures the X-ray profile of the patient and acquires a plurality of subviews of the patient attenuation data. Detector system 206 then sends the plurality of subviews of the patient attenuation data to computer 210. Computer 210 then processes the subviews to form saturation corrected subviews and thereafter, generates a cross-sectional image of the body of the patient based on the saturation corrected views. X-ray source 204 may radiate the X-ray beam of different intensities or radiation flux depending upon the input electrical energy to X-ray source 204. The electrical energy to X-ray source 204 is controlled by electrical energy controller 208. Modulation controller 212, in turn, generates timing signals to control electrical energy controller 208. Further, computer 210 is coupled to detector system 206 and modulation controller 212 and is programmed to control X-ray imaging system 200.

In various embodiments of the invention, X-ray source 204 includes an X-ray tube and an X-ray generator. The X-ray tube may have, for example, a cathode, and/or an anode source for generating an X-ray beam. The X-ray generator is the energy source that supplies the electrical energy and controls signals to the X-ray tube for generating the corresponding X-ray beam. The X-ray generator may be, for example, a single-phase X-ray generator, a three-phase X-ray generator, constant potential generator, and/or high-frequency inverter generator.

Detector system 206 is capable of detecting radiation flux within the dynamic range of detector system 206. For example, the radiation flux rates impinging on detector system 206 may range from about 2.5 thousand photons/sec/$mm^2$ to about 4 billion photons/sec/$mm^2$ and all sub-ranges therebetween, depending on scanner acquisition protocols and scanned patient anatomies. More specifically, detector system 206 may typically be exposed to 1.5 million photons/sec/$mm^2$ radiation flux for 1 mA at 120 kVp power. Detector system 206 communicates a response that is within a predetermined specification for relatively high X-ray flux and for relatively low X-ray flux. A portion of detector system 206 may saturate for values of radiation flux that lie outside the dynamic range. In various embodiments of the invention, detector system 206 may include, for example, xenon detectors, solid-state scintillator-photodiode detectors, direct conversion detectors, and/or single photon counting detectors, configured in multiple one-dimensional (single slice) or two-dimensional (multi-slice) detector arrays.

Computer 210 may include a data acquisition module 214 and a reconstruction module 216 that is communicatively coupled to a display 218. Data acquisition module 214 acquires a plurality of subviews of the patient attenuation data from detector system 206 and sends the acquired subviews to reconstruction module 216. Reconstruction module 216 then combines the subviews of the patient attenuation data to form saturation corrected views for subsequent cross-sectional image generation. The image is then displayed to the user of X-ray imaging system 200 on display 218.

Electrical energy controller 208 controls the electrical energy input to X-ray source 204. In various embodiments of the invention, electrical energy controller 208 controls the electrical energy input to the X-ray generator. The electrical energy input may, for example, be controlled by changing the input current (to the filament of the X-ray tube), and/or input voltage (to the X-ray generator). Electrical energy controller 208 may, for example, change the electrical energy input to X-ray source 204 in response to a user input, and/or in response to a command from modulation controller 212.

In various embodiments of the invention, electrical energy controller includes at least one of a current (referred to herein as mA) controller, and/or a high voltage controller. In one embodiment, the mA controller, for example, may change the input current to X-ray source 204, which in turn changes the radiation flux emitted by X-ray source 204. In another embodiment, the high voltage controller, for example, may change the input voltage level to X-ray source 204 which in turn changes the radiation flux emitted by X-ray source 204. In yet another embodiment, both the mA controller and the high voltage controller may together change the electrical energy input to X-ray source 204 by changing both the input current and input voltage. In various embodiments of the invention, an automatic mA control feature in known X-ray imaging system may be modified and used as an mA controller. The modification may be, for example, providing a means for switching from higher current level to lower current level at a faster rate.

Modulation controller 212 may be configured to generate timing signals to control electrical energy controller 208 by sending a command to switch the electrical energy input from a higher energy level to a lower energy level, or vice-versa. In various embodiments of the invention, modulation controller 212 may send a request for switching the electrical energy input from a higher energy level to a lower energy level, or vice-versa, at a pre-determined rate. In various embodiments of the invention, the switching of X-ray tube current may typically be in the range of 10-800 mA and all sub-ranges there between, with regulation of typically 10 percent along with compensation provided by an X-ray tube mA reference detector, an X-ray tube anode current monitor or an X-ray current monitor. In various embodiments of the invention, the switching of X-ray source high voltage may typically be in the range of 80-140 kVp and all sub-ranges there between, with regulation of typically 2 percent along with compensation provided by an X-ray tube kVp reference detector or tube kVp monitor.

In various embodiments of the invention, computer 210 may set the timing signal details of modulation controller 212 based on the selected scan.

In various embodiments of the invention, a grid structure may be incorporated between the X-ray tube filament and anode. The grid structure, along with control voltages connected to the grid structure, is used to switch an electron beam, liberated from the filament, between a higher radiation flux to a lower radiation flux. The grid structure may be used in addition or instead of known X-ray tube current controller, since the temporal response of the emission current from the X-ray tube filament using the known X-ray tube filament current controller is finite and for high current modulations the known X-ray tube current controller may not respond to the modulation requirements with sufficient speeds.

In various embodiments of the invention, while acquiring the plurality of subviews of the patient attenuation data (as described at 102), the first set of subviews of the patient attenuation data at the first (for example, higher) radiation flux level is acquired such that at least a portion of detector system 206 may be saturated and the second set of subviews of the patient attenuation data at the second (for example, lower) radiation flux level is acquired such that detector system 206 is likely not saturated. In various embodiments of the invention, the first radiation flux may be higher than second radiation flux.

In various embodiments of the invention, while acquiring the plurality of subviews of the patient attenuation data (as described at 102), the first set of subviews of the patient attenuation data at the first (for example, higher) radiation flux level is acquired such that at least a portion of detector system 206 is saturated and the second set of subviews of the patient attenuation data at the second (for example, lower) radiation flux level is acquired such that a lesser portion of detector system 206 is saturated.

In various embodiments of the invention, the electrical energy to X-ray source 204 is controlled between a first input current level and/or a first input voltage level corresponding to the first radiation flux level and a second input current level and/or a second input voltage level corresponding to the second radiation flux level.

In various embodiments of the invention, X-ray source 204 is switched between the first radiation flux level and the second radiation flux level at a predetermined rate. In various embodiments of the invention, the predetermined rate may be switching between the first radiation flux level and the second radiation flux level for every z subview of the patient attenuation data, wherein z is a positive number.

In various embodiments of the invention, x subviews of the patient attenuation data at the first radiation flux level are acquired for every y subviews of the patient attenuation data at the second radiation flux level, wherein x and y are positive numbers.

In various embodiments of the invention, while combining the first set of subviews data and the second set of subviews data to form saturation corrected views for subsequent image generation (as described at 104), the values in the saturated areas (i.e. where at least a portion of detector system 206 has saturated) of the first set of subviews of the patient attenuation data are estimated using the corresponding second set of subviews of the patient attenuation data values for each respective area to form saturation corrected views for subsequent image generation. In an embodiment, linear estimation is done to combine the first set of subviews and the second set of subviews of the patient attenuation data to form saturation corrected views for subsequent image generation. In another embodiment, non-linear estimation is done to combine the first set of subviews and the second set of subviews of the patient attenuation data to form saturation corrected views for subsequent image generation. In yet another embodiment, linear and/or non-linear estimation is done (for various iterative reconstruction methods or other non-filter back projection reconstruction methods) to combine the first set of subviews and the second set of subviews of the patient attenuation data to form saturation corrected views for subsequent image generation. In an exemplary embodiment, when switching is done between the first radiation flux level and the second radiation flux level by changing the X-ray tube current, and linear estimation is performed to form saturation corrected views for subsequent image generation. In this embodiment, linear estimation is performed because the radiation flux of X-ray source 204 varies linearly with the X-ray tube current. In another embodiment, switching is done between the first radiation flux level and the second radiation flux level by changing the input voltage to the X-ray generator, and non-linear estimation is performed to form saturation corrected views for subsequent image generation. In this embodiment, non-linear estimation is performed because the radiation flux of X-ray source 204 varies non-linearly with input voltage to the X-ray generator. In various embodiments of the invention, non-linear estimation is performed because of non-linear attenuation materials with respect to spectral shifts in radiating X-rays when the input voltage of X-ray generator is changed.

In various embodiments of the invention, the 1:1 ratio of low flux: high flux subviews may be increased. For example, every second set of subviews may be a low flux view (2:1 ratio). The estimation of saturated detector values is then done by interpolation between adjacent low flux subview values. Further, in various embodiments of the invention, switching between the first radiation flux level and the second radiation flux level is performed such that the acquisition time for the first radiation flux level is different than the acquisition time for the second radiation flux level. In an embodiment, the acquisition time for higher radiation flux level may be different than the acquisition time for lower radiation flux level. This may reduce the exposure time needed to collect the high-flux subviews the patient attenuation data due to reduction in number of high-flux subviews. Further, this may lead to reduced the X-ray radiation exposure to the patient.

In various embodiments of the invention, the 1:1 acquisition time ratio of low flux: high flux subviews may be decreased. The switching of the X-ray source between the first flux level and the second flux level may be either for subviews of equal or different duration at each level. For example, the acquisition time of the low level may be ¼ of the acquisition time of the high flux level. Further, the ratio may be either constant during the scan or varied according to the variation in the anatomy of the scanned patient.

In various embodiments of the invention, computer 210 modulates (through modulation controller 212) between the first radiation flux level and the second radiation flux level by monitoring saturation levels of detector system 206 and appropriately modifying the ratio of low flux subviews: high flux subviews and/or the acquisition timings. In an embodiment, saturation levels of detector system 206 may be monitored, for example, 'real time' or 'on line' during an operation of X-ray imaging system 200. In another embodiment, saturation levels of detector system 206 may be monitored by utilizing the pre-scan information from planar radiographic views.

Figure 3:
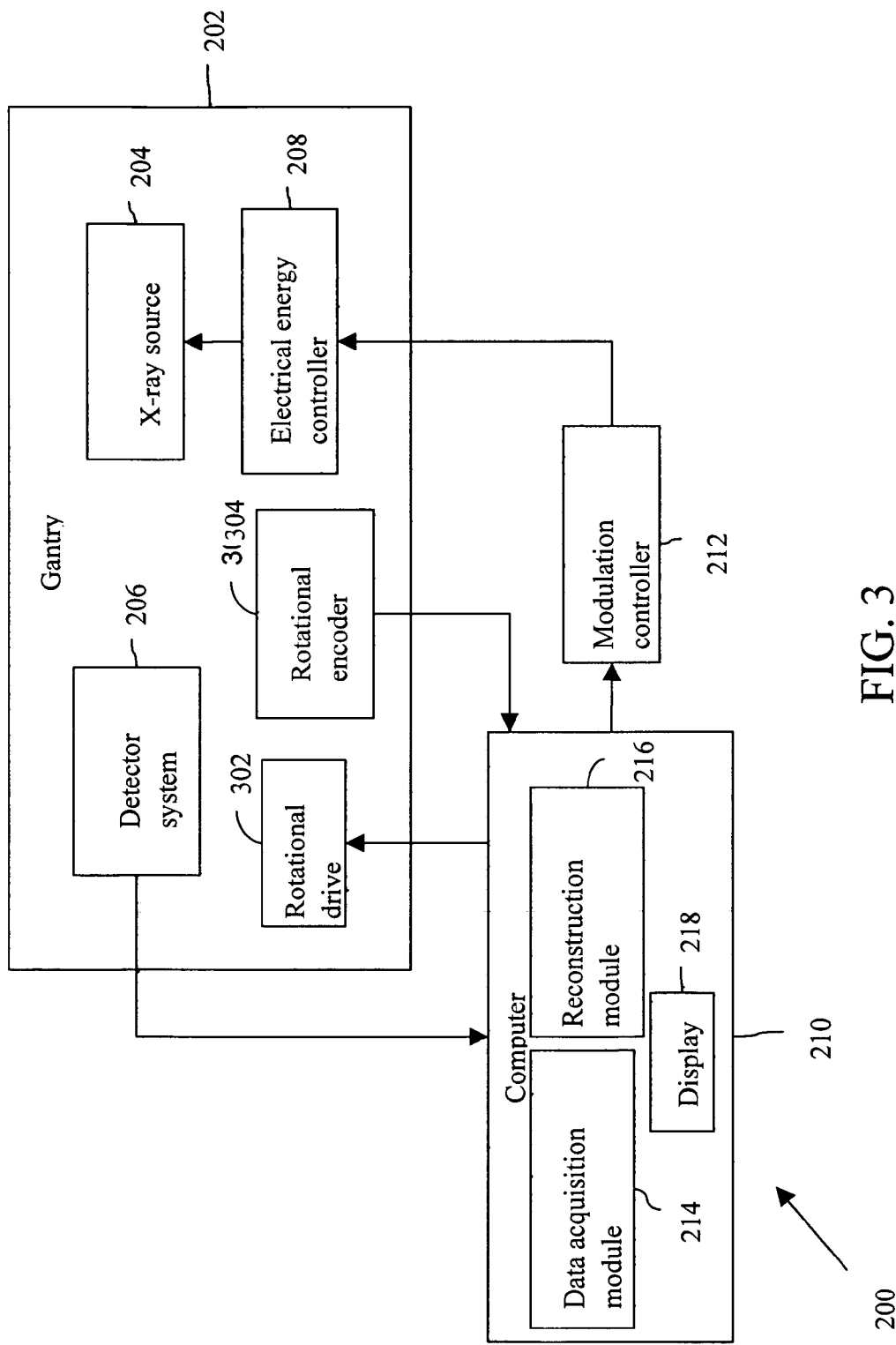
FIG. 3 is a block diagram of an X-ray imaging system in accordance with another embodiment of the invention.

FIG. 3 shows an X-ray imaging system 200 in accordance with another embodiment of the invention. Gantry 202 rotates X-ray source 204 and detector system 206 around a patient to perform a CT scan. Gantry 202 further includes a rotational drive 302 and a rotational encoder 304. In various embodiments of the invention, X-ray imaging system 200 may be a CT scanner.

Rotational drive unit 302 may rotate gantry 202 in response to an input from computer 210. Further, rotational drive unit 302 may provide a sweep of the X-ray beam around the patient. Rotational speeds of gantry 202 may typically be 0.3 to 4 seconds per 360° rotation of gantry 202. Further, rotational drive unit 302 may provide electron beam sweeping at the rate of 50 msec per 180° rotation sweep of gantry 202. Rotational drive unit 302 may include a direct drive, a belt drive, and AC, DC, servo and/or induction type motor. In various embodiments of the invention, the CT scanner may be a fifth generation CT scanner.

Rotational encoder 304 provides gantry angle information of gantry 202 to computer 210 to a precision of hundredths or thousandths of a degree. In various embodiments of the invention, rotational encoder 304 triggers detector system 206 and data acquisition module 214 through computer 210 to acquire plurality of subviews at particular gantry angles of gantry 202. In various embodiments of the invention, computer 210 may set timing signal information of modulation controller 212 based on the gantry angle information provided by rotational encoder 304. Rotational encoder 304 may be a electro-optical or a gear-driven assembly.

In various embodiments of the invention, the predetermined rate for angular sampling may be multiple times more rotation, for example, greater than 800 times per 360° rotation of gantry 202, and more specifically, greater than 1600 times per 360° rotation of gantry 202. In another embodiment of the invention, the predetermined rate may range from 800-10000, more specifically, 800-4000 times per 360° rotation of gantry 202. In various embodiments of the invention, the predetermined rate may, for example, acquire the first set of subviews of the patient attenuation data for at least 180° of rotation of gantry 202, and thereafter, switching X-ray source 204 from the first radiation flux level to the second radiation flux level. The second set of subviews of the patient attenuation data is then acquired for at least 180° of rotation of gantry 202. In various embodiments of the invention, the predetermined rate may be, for example, acquiring the first set of subviews of the patient attenuation data for every 'f1' fraction of degree and thereafter, switching X-ray source 204 from the first radiation flux level to the second radiation flux level, and acquiring the second set of subviews of the patient attenuation data for every 'f2' fraction of degree, where 'f1' and 'f2' may range from 0 to 360 and all sub-ranges there between. In various embodiments of the invention, the predetermined rate may be, for example, acquiring a first set of subviews of the patient attenuation data interleaved between acquiring a second set of subviews of the patient attenuation data, where cyclically a subview of the first set is acquired for every 'f3' fraction of degree and, and thereafter switching X-ray source 204 from the first radiation flux level to the second radiation flux level. The second set of subviews of the patient attenuation data is then acquired for every 'f4' fraction of degree, where 'f3' and 'f4' may or may not be equal fractions of a degree.

Figure 4:
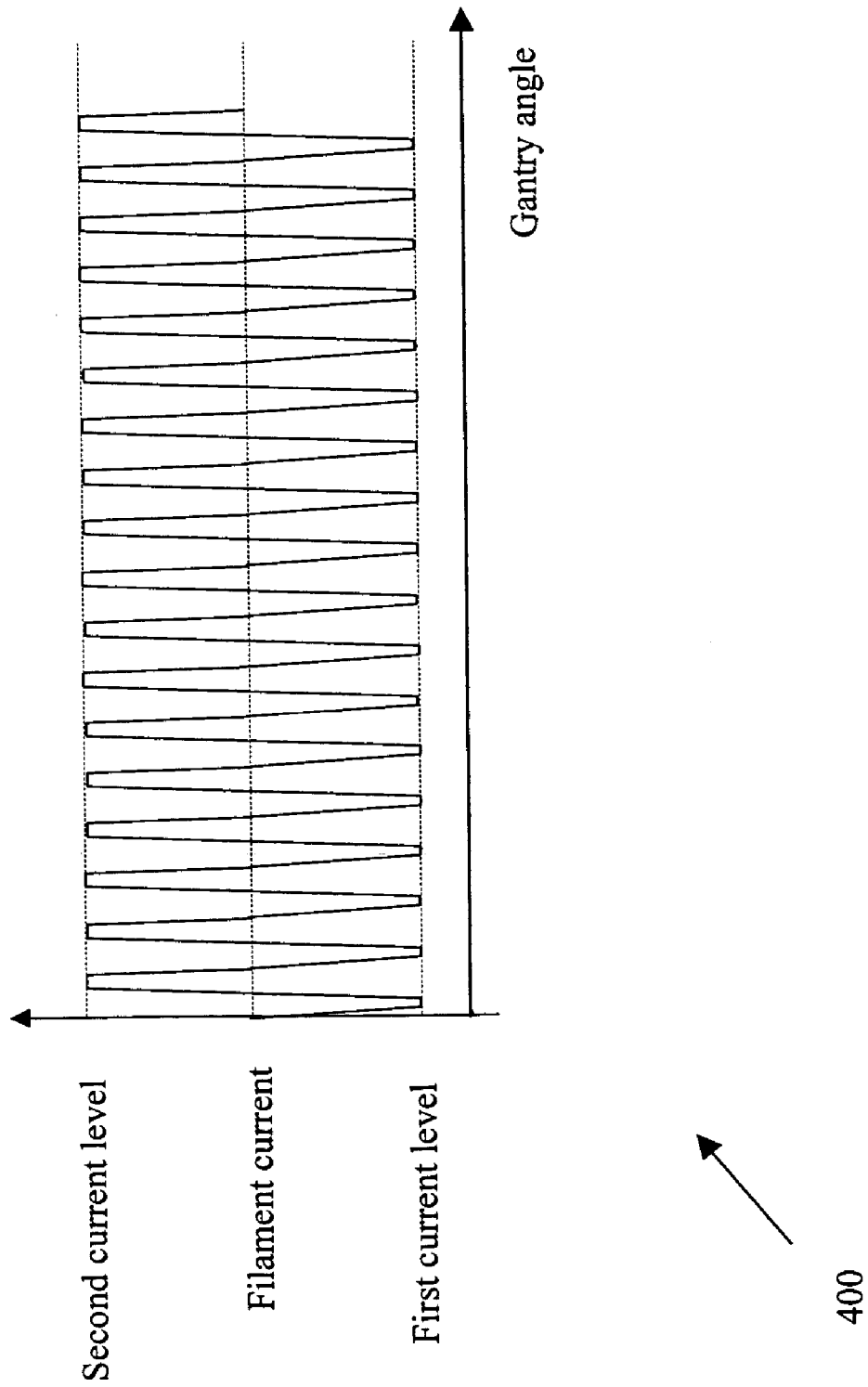
FIG. 4 shows a plot of an X-ray tube current versus a gantry angle in accordance with an exemplary embodiment of the invention.

FIG. 4 shows a plot 400 of the X-ray tube current versus the gantry angle in accordance with an exemplary embodiment of the invention. During a scan of X-ray imaging system 200 the X-ray tube current is switched between a first current level and a second current level at a predetermined rate of, for example, 1600 times per 360° rotation of gantry 202. The first current level is lower than the second current level. The switching between the first current level and the second current level, is performed by electrical energy controller 208, more specifically, by the mA controller in response to a request from modulation controller 212. Modulation controller 212 may request for the modulation in response to a request from computer 210. At the first current level, detector system 206 do not saturate, however, at the second current level a portion of detector system 206 may saturate. Since, response of detector system 206 is linear with current levels, therefore, while processing the subviews when computer 210 determines that a portion of detector system 206 may be saturated. Computer 210 estimates the corrected the patient attenuation data in the saturated area by multiplying the values in the area within the unsaturated areas in the first current level subview by a factor determined by the relative mA values used in the first current level and the second current level. Further, computer 210 replaces the saturated second current level values with the corresponding scaled first current level values. In an embodiment, the scaled first current level values are also added to the non-saturated second current level values. In an embodiment, where the patient attenuation data is not required in a view format (i.e. for various iterative reconstruction methods or other non-filter-back-projection reconstruction methods) linear and/or non-linear estimation may be done to combine the first set of subviews of the patient attenuation data and the second set of subviews of the patient attenuation data to estimate corrected patient attenuation data.

In various embodiments of the invention, if detector system 206 does not saturate both at the first radiation flux level and the second radiation flux level, then the first set of subviews of the patient attenuation data and the second set of subviews of the patient attenuation data may not be combined for subsequent image generation and are treated as additional independent subviews. The additional independent subviews may be appropriately weighted so as to contribute to increase in angular sampling and therefore, may be used to reduce image artifacts. In an embodiment of the invention, improved image quality and specifically improved image resolution, sampling resolution and/or low contrast resolution is possible by not combining the first set of subviews of the patient attenuation data and the second set of subviews of the patient attenuation data and subsequently preserving the high temporal sampling. For example, where saturated detector data need not be corrected, improved image quality may be achieved by either ignoring the low flux subviews entirely or by preserving independent high and low flux subviews and thereby, preventing reduction in the possible temporal sampling width.

Figure 5:
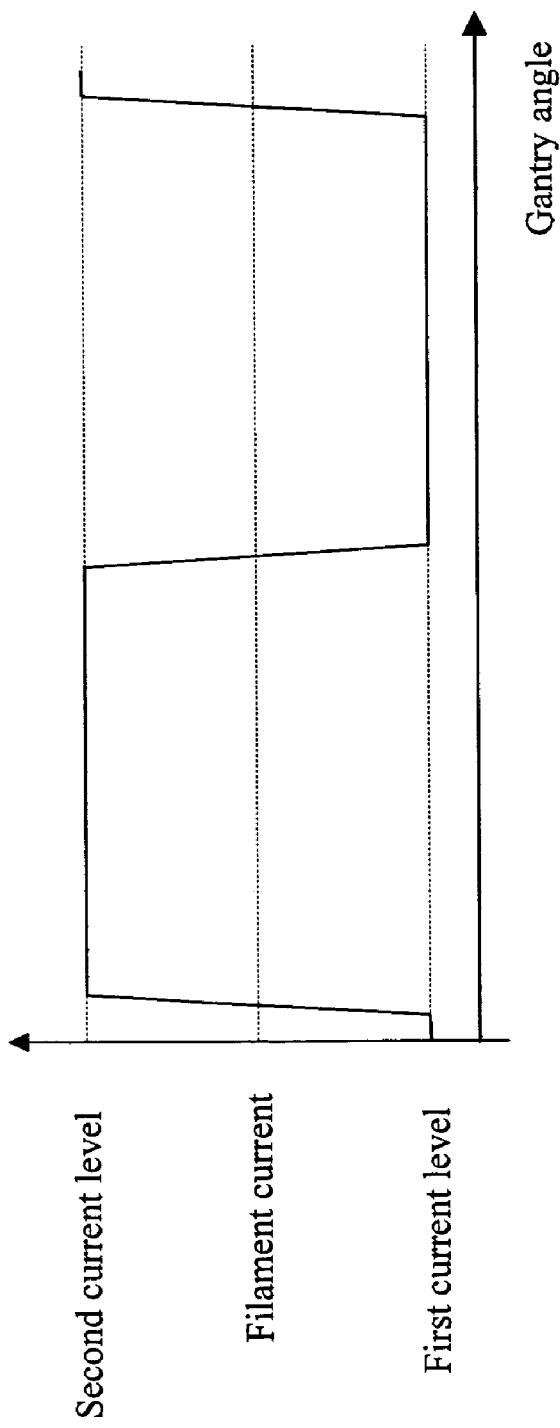
FIG. 5 shows a plot of an X-ray tube current versus a gantry angle in accordance with another embodiment of the invention.

FIG. 5 shows a plot 500 of the X-ray tube current versus the gantry angle in accordance with an exemplary embodiment of the invention. During a scan of X-ray imaging system 200 the X-ray tube current is switched between a low mA and a high mA at a predetermined rate of, for example, acquire the first set of subviews of the patient attenuation data at high mA for at least 180° of rotation of gantry 202, and thereafter, switching X-ray source 204 from high mA to low mA. The second set of subviews of the patient attenuation data at low mA is then acquired for at least 180° of rotation of gantry 202. The first current level is lower than the second current level. At the first current level, detector system 206 do not saturate, however, at the second current level a portion of detector system 206 may saturate. Since, response of detector system 206 is linear with current levels, while processing the subviews when computer 210 determines that a portion of detector system 206 may be saturated, computer 210 performs linear estimation between the 180 degree composite subviews to form a saturation-corrected set of views. In an embodiment where data is not required in 180 degree view format (i.e. for various iterative reconstruction methods or other non-filter-back-projection reconstruction methods) linear and/or non-linear estimation may be done to combine the first set of subviews of the patient attenuation data and the second set of subviews of the patient attenuation data to estimate corrected patient attenuation data.

In various embodiments of the invention, the radiation flux levels may be a plurality of radiation flux levels. In various embodiments of the invention, the radiation flux levels may be continuously changing radiation flux levels.

The various embodiments of the invention provide an X-ray imaging system that facilitates reducing the dynamic range requirements of known X-ray imaging detector technologies, thereby reducing the cost of the detector and/or permitting use of advanced detector configuration that are not capable of a large dynamic range. Further, various embodiments of the invention provide an X-ray imaging system that collects less the patient attenuation data (i.e., less bits per sample) and thereby, has lower data communication bandwidths and data storage requirements.

The various embodiments of the invention also provide an X-ray imaging system that enables reduction in the X-ray radiation exposure (to the patient) by monitoring saturation levels of the detector system and appropriately modifying the ratio of low flux subviews: high flux subviews and/or the acquisition timings.

A technical effect of the various embodiments of the invention is to reduce the stringent dynamic requirements of known X-ray imaging detector technologies. Another technical effect of the various embodiments of the invention is reduction in data communication bandwidths and data storage requirements.

The various embodiments or components thereof may be implemented as part of a computer system. The computer system may include a computer, an input device, a display unit and an interface, for example, for accessing the Internet. The computer may include a microprocessor. The microprocessor may be connected to a communication bus. The computer may also include a memory. The memory may include Random Access Memory (RAM) and Read Only Memory (ROM). The computer system further may include a storage device, which may be a hard disk drive or a removable storage drive such as a floppy disk drive, optical disk drive, and the like. The storage device can also be other similar means for loading computer programs or other instructions into the computer system.

As used herein, the term "computer" may include any processor-based or microprocessor-based system including systems using microcontrollers, reduced instruction set circuits (RISC), application specific integrated circuits (ASICs), logic circuits, and any other circuit or processor capable of executing the functions described herein. The above examples are exemplary only, and are thus not intended to limit in any way the definition and/or meaning of the term "computer".

The computer system executes a set of instructions that are stored in one or more storage elements, in order to process input data. The storage elements may also hold data or other information as desired or needed. The storage element may be in the form of an information source or a physical memory element within the processing machine.

The set of instructions may include various commands that instruct the processing machine to perform specific operations such as the processes of the various embodiments of the invention. The set of instructions may be in the form of a software program. The software may be in various forms such as system software or application software. Further, the software may be in the form of a collection of separate programs, a program module within a larger program or a portion of a program module. The software also may include modular programming in the form of object-oriented programming. The processing of input data by the processing machine may be in response to user commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

While the invention has been described in terms of various specific embodiments, those skilled in the art will recognize that the invention can be practiced with modification within the spirit and scope of the claims.

What is claimed is:

1. A method for controlling an X-ray imaging system that includes a gantry having a detector system and an X-ray source for radiating an X-ray beam along at least one of an imaging plane and a cone volume towards the detector system, said method comprising:
controlling an X-ray source current between a first current level corresponding to a first radiation flux level and a second current level corresponding to a second radiation flux level;
controlling the X-ray source high voltage between a first voltage level and a second voltage level based on a saturation level of the detector system;
acquiring a plurality of subviews of patient attenuation data wherein a first set of subviews of patient attenuation data is acquired at the first radiation flux level and a second set of subviews of patient attenuation data is acquired at the second radiation flux level, the first radiation flux level being different than the second radiation flux level; and
combining the first set of subviews of patient attenuation data and the second set of subviews of patient attenuation data to form corrected views for subsequent image generation.

2. A method in accordance with claim 1 wherein acquiring a plurality of subviews of patient attenuation data comprises acquiring the plurality of subviews of patient attenuation data wherein a plurality of sets of subviews of patient attenuation data is acquired at a respective radiation flux level for each set of subviews, each said respective radiation flux level being different than each other radiation flux level.

3. A method in accordance with claim 1 wherein acquiring a plurality of subviews of patient attenuation data comprises alternating between the first radiation flux level and the second radiation flux level during the acquisition.

4. A method in accordance with claim 1 wherein controlling an X-ray source current comprises at least one of controlling an X-ray tube filament current and a potential of an X-ray tube grid.

5. A method in accordance with claim 1 wherein controlling an X-ray source current comprises switching the X-ray source current between the first current level and the second current level at a predetermined rate.

6. A method in accordance with claim 1 wherein controlling an X-ray source current comprises switching the X-ray source current between the first current level and the second current level at a rate determined from a saturation level of the detector assembly.

7. A method in accordance with claim 1 wherein controlling an X-ray source current comprises switching the X-ray source current between the first current level and the second current level such that the acquisition time for the first current level is different than the acquisition time for the second current level.

8. A method in accordance with claim 1 wherein controlling an X-ray source current comprises switching the X-ray source current between the first current level and the second current level based on the saturation levels of the detector system.

9. A method in accordance with claim 5 wherein switching the X-ray source current between the first current level and the second current level at a predetermined rate comprises:
acquiring a first set of subviews of patient attenuation data for at least 180 degrees of rotation of the gantry;
switching the X-ray source current from the first current level to the second current level; and
acquiring a second set of subviews of patient attenuation data for at least 180 degrees of rotation of the gantry.

10. A method in accordance with claim 1 wherein acquiring a plurality of subviews of patient attenuation data comprises controlling at least one of an X-ray source current between a first current level corresponding to the first radiation flux level and a second current level corresponding to the second radiation flux level and controlling an X-ray source high voltage between a first voltage level corresponding to the first radiation flux level and a second voltage level corresponding to the second radiation flux level.

11. A method in accordance with claim 1 wherein acquiring a plurality of subviews of patient attenuation data comprises acquiring the first set of subviews of patient attenuation data at the first radiation flux level such that at least a portion of the detector system is saturated and acquiring the second set of subviews of patient attenuation data at the second radiation flux level such that the detector system is not saturated.

12. A method in accordance with claim 1 wherein acquiring a plurality of subviews of patient attenuation data comprises acquiring the first set of subviews of patient attenuation data at the first radiation flux level such that at least a portion of the detector system is saturated and acquiring the second set of subviews of patient attenuation data at the second radiation flux level such that a lesser portion of the detector system is saturated.

13. A method in accordance with claim 1 wherein combining the first set of subviews of patient attenuation data and the second set of subviews of patient attenuation data to form corrected views for subsequent image generation comprises estimating values in the saturated areas of the first set of subviews of patient attenuation data using the corresponding second set of subviews of patient attenuation data values for each respective area.

14. A method in accordance with claim 13 wherein estimating values in the saturated areas of the first set of subviews of patient attenuation data using the corresponding second set of subviews of patient attenuation data values for each respective area comprises using a linear estimation to combine the first set of subviews of patient attenuation data and the second set of subviews of patient attenuation data to form corrected views for subsequent image generation.

15. A method in accordance with claim 13 wherein estimating values in the saturated areas of the first set of subviews of patient attenuation data using the corresponding second set of subviews of patient attenuation data values for each respective area comprises using a non-linear estimation to combine the first set of subviews of patient attenuation data and the second set of subviews of patient attenuation data to form corrected views for subsequent image generation.

16. A method in accordance with claim 1 wherein acquiring a plurality of subviews comprises acquiring x subviews of patient attenuation data at the first radiation flux level for every y subview of patient attenuation data that is acquired at the second radiation flux level wherein x and y are positive integers.

17. A method in accordance with claim 1 wherein acquiring a plurality of subviews of patient attenuation data comprises controlling an X-ray source high voltage between a first voltage level corresponding to the first radiation flux level and a second voltage level corresponding to the second radiation flux level.

18. A method in accordance with claim 17 wherein controlling an X-ray source high voltage comprises switching the X-ray source high voltage between the first voltage level and the second voltage level at a predetermined rate.

19. A method in accordance with claim 17 wherein controlling an X-ray source high voltage comprises switching the X-ray source high voltage between the first voltage level and the second voltage level such that the acquisition time for the first voltage level is greater than the acquisition time for the second voltage level.

20. A method in accordance with claim 18 wherein switching the X-ray source high voltage between the first voltage level and the second voltage level at a predetermined rate comprises:
acquiring a first set of subviews of patient attenuation data for at least 180 degrees of rotation of the gantry;
switching the X-ray source high voltage from the first voltage level to the second voltage level; and
acquiring a second set of subviews of patient attenuation data for at least 180 degrees of rotation of the gantry.

21. A method in accordance with claim 1 wherein none of the first set of subviews and the second set of subviews is saturated.

22. A method in accordance with claim 1 further comprising:
acquiring a plurality of subviews of patient attenuation data at a plurality of different radiation flux levels wherein subviews acquired at substantially equal radiation levels comprise a set of subviews; and
combining the sets of subviews to form corrected views for subsequent image generation.

23. A method in accordance with claim 1 further comprising:
acquiring a plurality of subviews of patient attenuation data at a plurality of varying radiation flux levels wherein subviews acquired at substantially equal radiation levels comprise a set of subviews; and
combining the sets of subviews to form corrected views for subsequent image generation.

24. An X-ray imaging system comprising:
a gantry including a detector system and an X-ray source for radiating an X-ray beam along an imaging plane and/or volume towards the detector system;
at least one of mA controller, a grid potential controller, and a high voltage controller for controlling electrical energy to the X-ray source;
a modulation controller communicatively coupled to said at least one of the mA controller, the grid potential controller, and the high voltage controller, said modulation controller configured to generate timing signals for controlling said at least one of the mA controller, the grid potential controller, and the high voltage controller; and
a computer coupled to the X-ray source and the gantry, said computer programmed to control the X-ray imaging system to:
control at least one of an X-ray source current, an X-ray source high voltage, and an X-ray source control grid potential between a first level corresponding to a first radiation flux level and a second level corresponding to a second radiation flux level;
switch at least one of the X-ray source current and the X-ray source high voltage between the first level and the second level based on the saturation levels of the detector system;
acquire a plurality of subviews of patient attenuation data wherein a first set of subviews of patient attenuation data is acquired at a first radiation flux level and a second set of subviews of patient attenuation data is acquired at a second radiation flux level, the first radiation flux level being different than the second radiation flux level; and
combine the first set of subviews of patient attenuation data and the second set of subviews of patient attenuation data to form corrected views for subsequent image generation.

25. An X-ray imaging system in accordance with claim 24 wherein said computer is further programmed to switch at least one of the X-ray source current, the X-ray source high voltage, and the X-ray source control grid potential between the first level and the second level at a predetermined rate.

26. An X-ray imaging system in accordance with claim 25 wherein said computer is further programmed to:
acquire a first set of subviews of patient attenuation data for at least 180 degrees of rotation of the gantry;
switch at least one of the X-ray source current and the X-ray source high voltage from the first level to the second level; and
acquire a second subview of patient attenuation data for at least 180 degrees of rotation of the gantry.

27. An X-ray imaging system in accordance with claim 24 wherein said computer is further programmed to switch at least one of the X-ray source current and the X-ray source high voltage between the first level and the second level such that the acquisition time for the first level is greater than the acquisition time for the second level.

28. An X-ray imaging system in accordance with claim 24 wherein the X-ray imaging system further comprises a rotational drive unit, the rotational drive unit rotating the gantry in response to an input from said computer.

29. An X-ray imaging system in accordance with claim 24 wherein the X-ray imaging system further comprises a rotational encoder, the rotational encoder providing gantry angle information to said computer.

30. An X-ray imaging system in accordance with claim 29 wherein said computer is further programmed to set timing signals of said modulation controller based on the gantry angle information.

31. An X-ray imaging system in accordance with claim 24 wherein said computer is further programmed to:
   acquire a plurality of subviews of patient attenuation data at a plurality of different radiation flux levels wherein subviews acquired at substantially equal radiation levels comprise a set of subviews; and
   combine the sets of subviews to form corrected views for subsequent image generation.

32. An X-ray imaging system in accordance with claim 24 wherein said computer is further programmed to:
   acquire a plurality of subviews of patient attenuation data at a plurality of varying radiation flux levels wherein subviews acquired at substantially equal radiation levels comprise a set of subviews; and
   combine the sets of subviews to form corrected views for subsequent image generation.

33. A computer program embodied on a computer readable medium for controlling an X-ray imaging system, the system having a gantry including a detector system and an X-ray source for radiating an X-ray beam along an imaging plane and/or volume towards the detector system, a modulation controller configured to generate timing signals for controlling said X-ray source, said program comprising a code segment that controls a computer that:
   controls at least one of an X-ray source current and an X-ray source high voltage between a first level and a second level based on a saturation level of the detector system;
   acquires a plurality of subviews of patient attenuation data wherein a first set of subviews of patient attenuation data is acquired at the first radiation flux level and a second set of subviews of patient attenuation data is acquired at the second radiation flux level, the first radiation flux level being different than the second radiation flux level; and
   combines the first set of subviews of patient attenuation data and the second set of subviews of patient attenuation data to form corrected views for subsequent image generation.

34. A computer program in accordance with claim 33 wherein no saturated areas of the first subview of data exist and first and second subview data are used independently or combined to improve sampling resolution that facilitates improved image quality.

35. A computer program in accordance with claim 33 wherein no saturated areas of the first subview of data exist and first and second subview data are used independently or combined to improve low contrast resolution that facilitates improved image quality.

36. A computer program in accordance with claim 33 further comprising a code segment that controls at least one of an X-ray source current and an X-ray source high voltage between a first level corresponding to the first radiation flux level and a second level corresponding to the second radiation flux level.

37. A computer program in accordance with claim 33 further comprising a code segment that controls at least one of the X-ray source current and the X-ray source high voltage between the first level and the second level such that the acquisition time for the first level is greater than the acquisition time for the second level.

38. A computer program in accordance with claim 33 further comprising a code segment that switches at least one of the X-ray source current and the X-ray source high voltage between the first level and the second level at a predetermined rate.

39. A computer program in accordance with claim 33 further comprising a code segment that:
   acquires a first set of subviews of patient attenuation data for at least 180 degrees of rotation of the gantry;
   switches at least one of the X-ray source current and the X-ray source high voltage from the first level to the second level; and
   acquires a second set of subviews of patient attenuation data for at least 180 degrees of rotation of the gantry.

40. A computer program in accordance with claim 33 further comprising a code segment that switches at least one of the X-ray source current and the X-ray source high voltage between the first level and the second level multiple times per rotation of the gantry.

41. A computer program in accordance with claim 33 further comprising a code segment that switches at least one of the X-ray source current and the X-ray source high voltage between the first level and the second level one or more times per rotation of the gantry.

42. A computer program in accordance with claim 33 further comprising a code segment that acquires the first set of subviews of patient attenuation data at the first radiation flux level such that at least a portion of the detector system is saturated and acquires the second set of subviews of patient attenuation data at the second radiation flux level such that the detector system is not saturated.

43. A computer program in accordance with claim 33 further comprising a code segment that acquires the first set of subviews of patient attenuation data at the first radiation flux level such that at least a portion of the detector system is saturated and acquires the second set of subviews of patient attenuation data at the second radiation flux level such that a lesser portion of the detector system is saturated.

44. A computer program in accordance with claim 33 further comprising a code segment that estimates values in the saturated areas of the first set of subviews of patient attenuation data using the corresponding second set of subviews of patient attenuation data values for each respective area.

45. A computer program in accordance with claim 33 further comprising a code segment that uses a linear estimation to combine the first set of subviews of patient attenuation data and the second set of subviews of patient attenuation data to form corrected views for subsequent image generation.

46. A computer program in accordance with claim 33 further comprising a code segment that uses a non-linear estimation to combine the first set of subviews of patient attenuation data and the second set of subviews of patient attenuation data to form corrected views for subsequent image generation.

47. A computer program in accordance with claim 33 further comprising a code segment that acquires a plurality of subviews of patient attenuation data at the first radiation flux level for every x subview of patient attenuation data that is acquired at the second radiation flux level wherein x is a positive number.

48. A computer program in accordance with claim 33 further comprising a code segment that switches the X-ray source current alternately between the first radiation flux level and the second radiation flux level for subviews of equal or different acquisition time at each level.

49. A computer program in accordance with claim 33 wherein the first set of subviews of the patient attenuation data include saturated areas, said computer program further comprising a code segment that uses at least one of the first set of subviews of the patient attenuation data and second set of subviews of the patient attenuation data together or independently to facilitate improving a sampling resolution.

50. A computer program in accordance with claim 33 wherein the first set of subviews of the patient attenuation data include saturated areas, said computer program further comprising a code segment that uses at least one of the first set of subviews of the patient attenuation data and second set of subviews of the patient attenuation data together or independently to facilitate improving at least one of a materials differentiation and a low contrast resolution.

51. A computer program in accordance with claim 33 wherein said computer is further programmed to:
  acquire a plurality of subviews of patient attenuation data at a plurality of different radiation flux levels wherein subviews acquired at substantially equal radiation levels comprise a set of subviews; and
  combine the sets of subviews to form corrected views for subsequent image generation.

52. A computer program in accordance with claim 33 wherein said computer is further programmed to:
  acquire a plurality of subviews of patient attenuation data at a plurality of varying radiation flux levels wherein subviews acquired at substantially equal radiation levels comprise a set of subviews; and
  combine the sets of subviews to form corrected views for subsequent image generation.

* * * * *

UNITED STATES PATENT AND TRADEMARK OFFICE
CERTIFICATE OF CORRECTION

PATENT NO. : 7,649,974 B2 Page 1 of 1
APPLICATION NO. : 10/993705
DATED : January 19, 2010
INVENTOR(S) : Arenson et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1462 days.

Signed and Sealed this

Twenty-third Day of November, 2010

David J. Kappos
*Director of the United States Patent and Trademark Office*